United States Patent [19]

Metrick

[11] 4,337,780
[45] Jul. 6, 1982

[54] MUSCLE TESTING APPARATUS

[76] Inventor: Glen F. Metrick, 2366 E. Mall Dr., Apt. 515, Ft. Myers, Fla. 33901

[21] Appl. No.: 148,307

[22] Filed: May 9, 1980

[51] Int. Cl.³ .............................................. A61B 5/10
[52] U.S. Cl. ...................................... 128/774; 73/379
[58] Field of Search .................... 128/59, 60, 28, 774; 73/379

[56] References Cited

U.S. PATENT DOCUMENTS

| 505,745 | 9/1893 | Barclay | 128/60 |
| 4,144,877 | 3/1979 | Frei et al. | 128/774 |
| 4,250,894 | 2/1981 | Frei et al. | 128/774 |

FOREIGN PATENT DOCUMENTS

| 44569 | 5/1961 | Poland | 128/774 |

Primary Examiner—Lee S. Cohen
Assistant Examiner—Nancy A. B. Swisher
Attorney, Agent, or Firm—Leitner, Palan, Martin & Bernstein

[57] ABSTRACT

A technique and apparatus for muscle strength testing. A gauged pressure sensitive device is applied to the muscle while pressure to the muscle is gradually increased to a point just short of the muscle breaking point. The applied pressure at this pre-breaking point is measured to provide an objective measure of muscle strength. The gauged pressure sensitive device may be an air bag connected to a pressure gauge, the air bag being placed between the pressure source and the muscle, thereby allowing the applied pressure to be measured.

8 Claims, 6 Drawing Figures

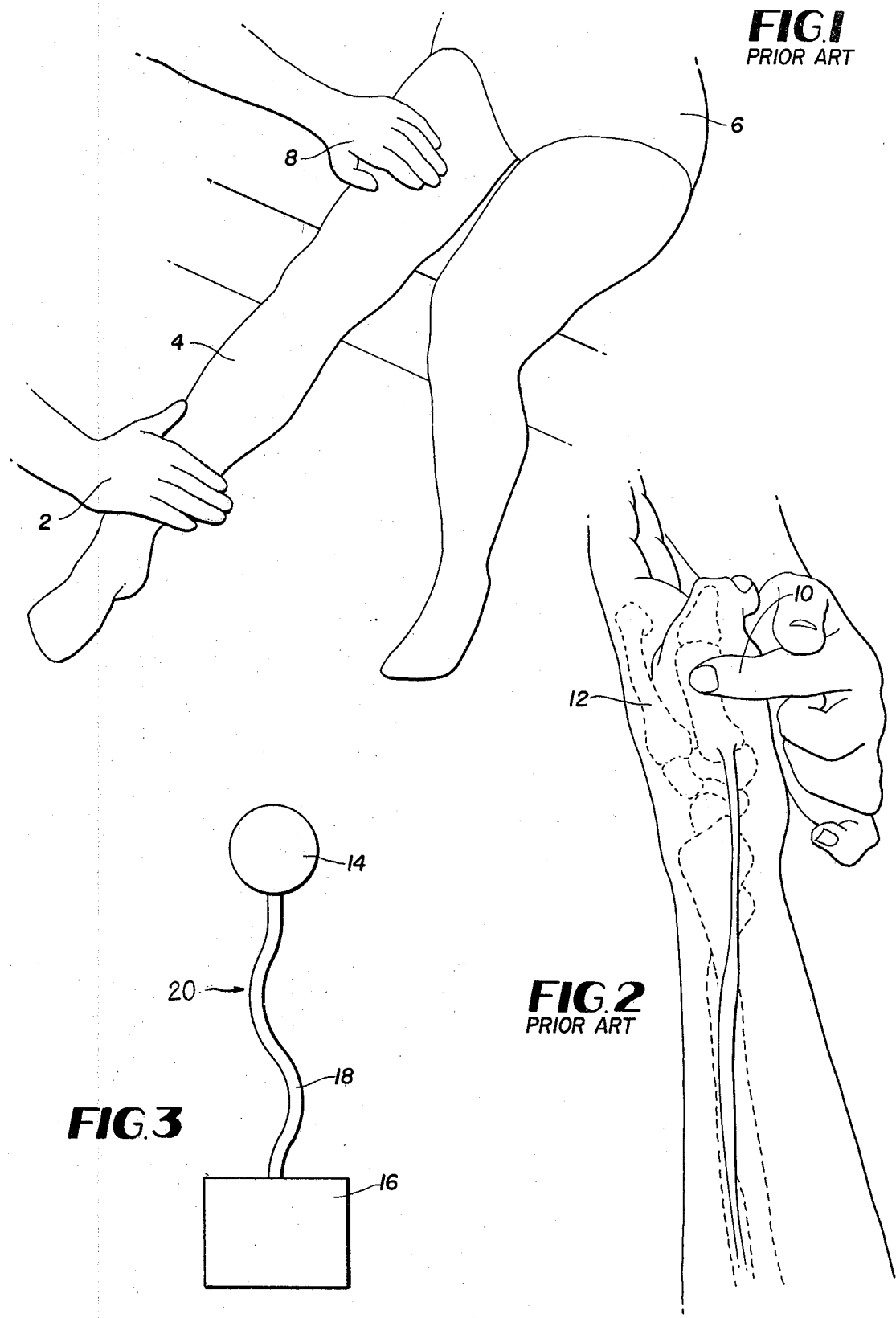

MUSCLE TESTING APPARATUS

BACKGROUND OF THE INVENTION

The present invention relates generally to the field of physical therapy and more particularly to the objective testing of muscle strength.

In the field of physical therapy a proper physical examination is of utmost importance in determining the type of therapy a patient will receive and, further, on how well that patient is responding to his or her therapy. In addition, muscle testing is an important and integral part of a physical examination as it provides information, not otherwise obtained, useful in differential diagnosis, prognosis, and treatment of neuromuscular and musculoskeletal disorders. Since, many neuromuscular conditions are characterized by muscle weakness, it becomes very important to determine which muscles are weak and the extent of that weakness.

In performing a muscle test, it is the standard procedure to position the patient in the proper position for the desired muscle response. The position is important in relation to the test in two respects: (1) In so far as practical, the position of the body should permit function against gravity for all muscles in which gravity is a factor in grading, and (2) the body should be in such a position that parts not being tested will be held as firm and stable as possible.

After the patient is in proper position, the physical therapist or tester administers the muscle test by applying gradually increasing pressure to the muscle under test. The term "pressure" as used herein denotes the outside force applied by the examiner to the muscle. Although the place where pressure is applied is significant to the accuracy of the testing, a very important aspect of the test is the evaluation of the amount of pressure applied by the tester. The amount of applied pressure varies according to the size of the patient and the muscle being tested. The patient must be allowed to "set" or contract his muscles against the tester's pressure. The tester cannot gauge the degree of strength unless pressure is applied gradually because slight pressure applied suddenly can "break" or over come the pull of the muscle.

It is standard procedure for therapists or examiners to grade the strength of a tested muscle. By conventional standards the ability of a patient to hold his muscle in a test position against the force of gravity establishes a grade factor of 50% or fair. The examiner then applies pressure to determine grades above 50%. The amount of pressure applied by the examiner in testing is the determining factor in grading above 50%. Under present testing procedures and due to the subjectiveness of measuring the applied pressure, the muscle strength of a patient can only be expressed as the ability of a muscle to hold against a minimum, moderate, or maximum amount of applied pressure. A minimum amount is given a grade of 60% to 70%, a moderate amount indicates a grade of 80% to 90% and a maximum amount results in a grade of 100%. Strong pressure is necessary to reach the 100% grade and because to much applied pressure can result in injury to the muscle, testers are justifiably reluctant to continue the muscle strength test to the maximum or 100% point.

During the course of the muscle testing procedure, a point, termed the breaking point, is reached at which the muscle can no longer counteract the external forces of gravity plus the tester's applied pressure and the muscle being tested moves in a direction which does not oppose the applied forces. Because muscle injury can occur to the muscle if the breaking point is reached, testers base their diagnoses and prognoses of muscle condition on the amount of the applied pressure at a point of muscle reaction just prior to the breaking point called the pre-breaking point. It is at this pre-breaking point that the muscle is "graded".

As is evident by the above description of conventional muscle testing the current testing procedures involve two subjective determinations made by the tester during the course of the test:

(1) the instant of time at which the pre-breaking point is reached and (2) the evaluation of the amount of pressure being applied at the instant the pre-breaking point is reached.

The present invention is directed to eliminating the subjective nature of the evaluation of the amount of pressure being applied at the instant the pre-breaking point is reached.

SUMMARY OF THE INVENTION

According to the invention there is provided a technique for more objectively evaluating muscle strength, which technique includes applying a pressure sensitive device to the muscle under test, gradually increasing applied pressure to the muscle until the pre-breaking point is reached and using the pressure sensitive device evaluating the amount of pressure so applied.

According to the invention there is further provided an apparatus that can be used to perform the above described method.

In one embodiment, the inventive apparatus consists of an air-tight bag like device operatively connected to a pressure responsive device by flexible tubing. The air-tight bag and pressure gauge are provided with any suitable means such as elastic strips or the like for appropriately attaching the air-tight bag and pressure gauge to the hand of the tester.

In another embodiment, the inventive apparatus consists of a small air-tight bag, a larger air-tight bag, a two-way valve, and a pressure responsive device all operatively connected by flexible tubing. The small air-tight bag is provided with elastic bands for attaching the small air-tight bag to the palmer side of the distal end of the index finger of the person performing the muscle test. The larger air-tight bag is provided with elastic bands for attaching said larger air-tight bag to the palm of the tester's hand. Both the pressure responsive device and two-way valve are likewise provided with elastic bands so that they may be attached to the dorsal side of the tester's hand. The flexible tubing operatively connects the small air-tight bag, the large air-tight bag, the pressure responsive device and two-way valve so that the tester can operate the two-way valve to selectively connect either the small air-tight bag or large air-tight bag to the pressure responsive device.

In still another embodiment, the inventive apparatus is in the form of a glove to be worn on the hand of the tester. A small air-tight bag is attached to the exterior of the glove at the place that the distal palmer surface of the tester's index finger would ordinarily be located. A large air-tight bag is sewn onto the exterior of the palm surface of the glove. The two-way valve and the pressure responsive device are mounted on the dorsal surface of the hand. The air-tight bags, two-way valve and pressure responsive device are operatively interconnected by tubing similarly as described in the prior embodiment.

A physical therapist using the inventive apparatus to test individual muscles can determine the pressure, measured in quantitative units, applied to the patient's muscle to reach the pre-breaking point thereof.

Other objects, advantages, and novel features of the present invention will become apparent from the following detailed description of the invention when considered in conjunction with the accompany drawings.

BRIEF DESCRIPTION OF DRAWINGS

FIG. 1 illustrates a prior art typical test of a leg muscle by a tester of a patient without the use of the invention in which pressure is applied by the right hand palm of the tester.

FIG. 2 illustrates a prior art typical test of a hand muscle by a tester without the use of the invention in which pressure is applied to the muscle to be tested by the index finger of the tester.

FIG. 3 is a plan view of one embodiment of a testing apparatus employing the principles of the inventive concept.

DETAILED DESCRIPTION OF THE PREFERRED EMBODIMENT OF THE INVENTION

Figure 4:
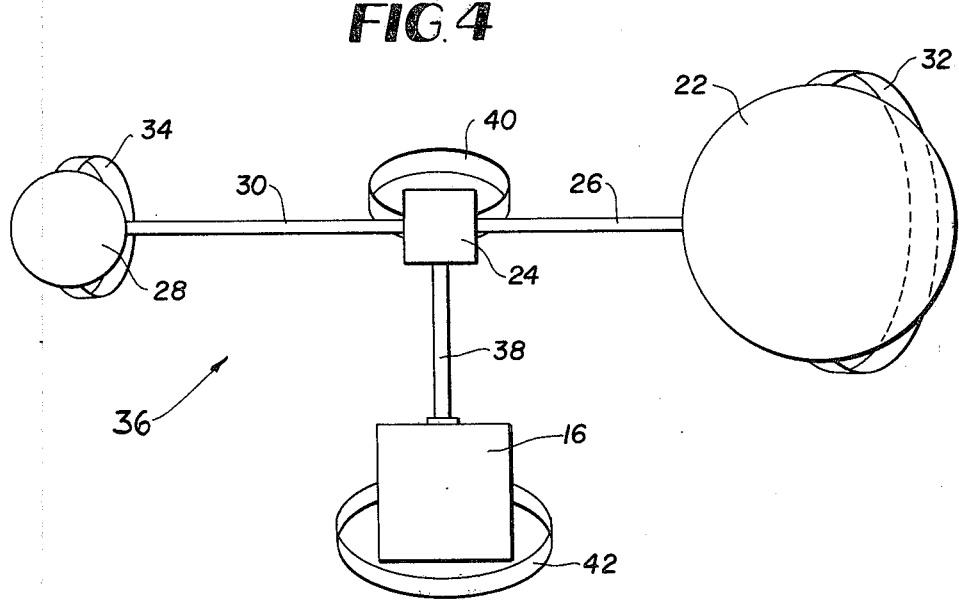
FIG. 4 is a plan view of another embodiment of a testing apparatus employing the principles of the inventive concept.

FIGS. 1 and 2 illustrate typical prior art examples employed by physical therapists or testers to test the strength of individual muscles of a patient. In FIG. 1 the palm of the right hand 2 of the tester is shown applying pressure against the leg 4 of the patient 6 above the ankle in a downward direction. Left hand 8 of the tester is shown stabilizing leg 4 of the patient. In FIG. 2 the index finger 10 of the tester is shown applying pressure against the lateral surface of the distal end of the first metacarpal of the patient's hand 12. In both of the tests illustrated in FIGS. 1 and 2 once sufficient pressure has been applied by the tester to reach the pre-breaking point of the muscle being tested, the tester must subjectively evaluate the amount of that applied pressure so that a diagnosis or prognosis of the strength of the muscle can be made. It can be appreciated that an accurate evaluation is difficult. Further, without the use of the inventive apparatus if a subsequent test is performed by another tester on the same muscle, there is no way for the second tester's evaluation of the amount of applied pressure necessary to reach the pre-breaking point to be objectively compared with the evaluation made by the first tester.

Referring to FIG. 3, the elements used in a simplied version of the inventive appartus 20 are shown in plan view. Air-tight bag 14 of any suitable material is operatively connected to a pressure responsive device 16 by tubing 18 to form an air-tight compartment. An amount of air sufficient to inflate air-tight bag 14 when the testing apparatus 20 is in an at-rest or inactive position is initially placed in the air-tight compartment. Pressure responsive device 16 may be any suitable device commercially available used to measure air pressure such as a sphygmonanometer.

In operation, air-tight bag 14 is placed over the insertion of the muscle to be tested. Referring to FIGS. 1 and 2, the bag 14 would be placed between the tester's hand and the patient's body. The tester (not shown) gradually applies pressure to bag 14. The increasing pressure causes a decrease in the volume of bag 14 resulting in increased pressure within the air-tight compartment made up of the bag, tubing, and pressure responsive device 16. At the instant the tester senses that the pre-breaking point of the muscle being tested has been reached the reading on pressure-sensitive device is noted. It will be appreciated that the quantitative value of pressure to reach the pre-breaking point is thus determined. The use of the same apparatus by a second tester would result in the same quantitized reading at the instant that the pre-breaking point of the muscle under test is reached.

Referring to FIG. 4, the elements used in another embodiment of the inventive muscle testing apparatus are shown in plan view. Muscle testing apparatus 36 is comprised of air-tight bag 22 connected to a two-way value 24 by flexible tubing section 26. Two-way valve 24 may be the type commercially available. Air-tight bag 28 is connected to valve 24 by flexible tubing section 30. Attached to air bag 22 is elastic strap 32. Attached to air-tight bag 28 is elastic strap 34. Pressure responsive device 16 is connected to valve 24 by flexible tubing section 38. Attached to valve 24 and pressure responsive device 16 are elastic straps 40 and 42 respectively.

The operation of the inventive muscle tester 36 illustrated in FIG. 4 can be explained as follows. Two-way valve 24 has two operating positions. In the first operating position a first air-tight section is formed comprising air bag 28, flexible tubing sections 30 and 38 and pressure-responsive device 16. In an at-rest or inactive position there is sufficient initial pressure in the first air-tight section so that air-bag 28 is inflated. As external pressure is applied to air-tight bag 28 the internal pressure of the air-tight compartment is increased and the air in bag 28 is forced through tubing 30, valve 24, tubing 38 into pressure responsive device 16 to produce a quantitized reading of pressure directly related to the amount of pressure applied.

Valve 24 can be placed in its second operating position so that a second air-tight section is formed comprising air bag 22, flexible tubing sections 26 and 38 and pressure responsive device 16. In its at-rest or inactive position there is sufficient air pressure in the second air-tight section so that air bag 22 is inflated. As external pressure is applied to air-bag 22 the internal pressure of the second air-tight section is increased and the air in bag 22 is forced through tubing 26 and 38 into pressure responsive device 16 to produce a quantitized reading of pressure directly related to the amount of pressure applied.

In practice, the muscle tester 36 is worn on the hand of the tester such that air-bag 28 is secured to the distal palmer surface of the tester's index finger by elastic band or strap 34. Air-bag 22 is secured to the tester's palm by elastic band or strap 32. Valve 24 and pressure responsive device 16 is secured to the dorsal or back of the tester's hand by elastic band or straps 40 and 42 respectively. To perform a test as shown in FIG. 1 wherein the tester must use the palm of his hand in the testing procedure, the tester must set the two-way valve so that the second air-tight section as described above is formed. As the tester applies gradually increasing pressure on the leg muscle of the patient, air bag 22 will be compressed and the internal pressure in the air-tight section increased. The tester will continue to apply pressure until the pre-breaking point of the muscle is reached. At the instant the pre-breaking point is reached the reading on the pressure sensitive device 16 can be noted and the amount of pressure needed to reach the muscle pre-breaking point quantitatively determined. It can be appreciated that a subsequent test preformed by another tester on the same patient should result in the same reading of applied pressure necessary to reach the muscle pre-breaking point.

Figure 5:
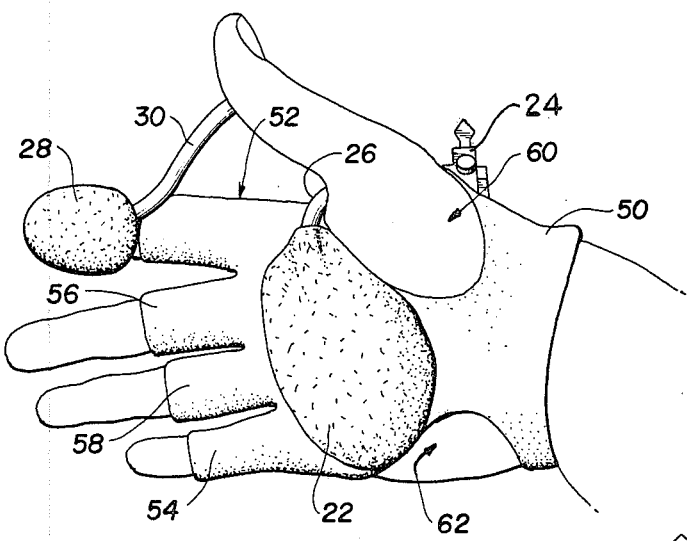
FIG. 5 is a plan view of the palm side of a glove incorporating the principles of the present invention.
Figure 6:
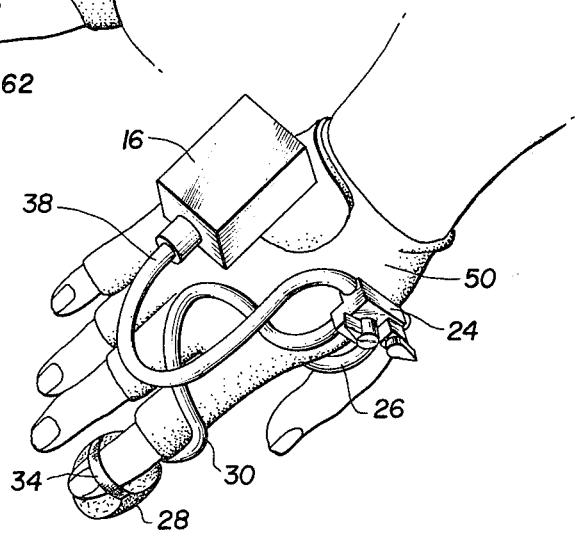
FIG. 6 is a plan view of the dorsal side of a glove incorporating the principals of the present invention.

An alternative embodiment of the invention is disclosed in FIGS. 5 and 6 wherein a glove 50 made of any suitable material is specifically constructed to operatively employ all the elements of the invention. FIG. 5 is a plan view of the exterior of the surface of the palm side of glove 50 worn on the right hand of a tester. Glove 50 is constructed with fingers 52, 54, 56 and 58 and two-thumb holes 60 and 62. The thumb holes 60 and 62 are provided so that the glove may be worn and used on either the right hand or left hand of the tester. In FIGS. 5 and 6 the element of the muscle tester have been mounted on glove 50 so that the glove can be used on the right-hand of the tester.

Air-tight bag 22 is permanently mounted, by sewing or other suitable means, to the palm section of glove 50 as shown. Flexible tubing section 26 is positioned so that it extends from air-tight bag 22 between thumb-hole 60 and index figure 52 of glove 50. In use, air-tight bag 28 is removably mounted by elastic strap 34 to the palm side of the index finger of the tester as shown in FIGS. 5 and 6. Flexible tubing 30 extends out of air-tight bag 28 as illustrated. As shown in FIG. 6 flexible tubing section 26 and 30 are connected to two-way valve 24 mounted on the dorsal side of glove 50. Also positioned on the dorsal side of glove 50 and next to valve 24 is pressure sensitive device 16 operatively connected to valve 24 by flexible tubing 38.

It will be obvious that an examiner testing the individual muscle of a patient as shown in FIGS. 1 and 2 can wear either the muscle tester apparatus as described in FIG. 4 or the muscle testing glove 50 described in FIGS. 5 and 6.

From the preceding description of the preferred embodiments, it is evident that the invention described herein results in an apparatus in which the previous subjective determination of the amount of pressure applied by a tester to reach the pre-breaking point of a patient's muscle under test can be measured in a quantitative amount. Although the invention has been described and illustrated in detail, it is to be clearly understood that the same is by way of illustration and example only and is not to be taken by way of limitation. The spirit and scope of this invention is to be limited only by the terms of the appended claims.

I claim:

1. An apparatus for objectively evaluating the amount of pressure needed to reach the pre-breaking point of a muscle of an individual during the course of a muscle strength test comprising:
    first pressure sensitive means for sensing the pressure applied to a muscle;
    second pressure sensitive means for sensing the pressure applied to a muscle;
    pressure responsive means for indicating the pressure sensed by said first or second pressure sensitive means; and
    means interconnecting said first and second pressure sensitive means to said pressure responsive means for selectively interconnecting said first or said second pressure sensitive means to said pressure responsive means.

2. The apparatus of claim 1, wherein said first pressure sensitive means has a greater surface area to be in contact with said muscle than said second pressure sensitive means for testing larger muscles than said second pressure sensitive means.

3. The apparatus of claim 1 including means for mounting said first and second pressure sensitive means to the hand of the person performing said muscle test.

4. The apparatus of claim 1, wherein said first and second pressure sensitive means are fluid filled bags and said selectively interconnecting means is a valve.

5. A muscle testing glove comprising: a glove,
    first pressure sensitive means permanently mounted on the exterior palm surface of said glove;
    second pressure sensitive means adapted to be removably mounted over the distal palmer surface of one of the glover wearer's fingers;
    pressure responsive means mounted on the exterior dorsal surface of said glove for indicating the pressure sensed by said first or second pressure sensitive means;
    means interconnecting said first and second pressure sensitive means and said pressure responsive means and mounted on the exterior dorsal surface of said glove for selectively interconnecting said first or second pressure sensitive means to said pressure responsive means.

6. The muscle testing glove of claim 5, wherein said first pressure sensitive means has a greater surface area to be in contact with said muscle than said second pressure sensitive means for testing larger muscles than said second pressure sensitive means.

7. The muscle testing glove of claim 5, wherein said first and second pressure sensitive means are fluid filled bags and said selectively interconnecting means is a valve.

8. The muscle testing glove of claim 5 wherein said glove has four finger portions and two hole portions, said hole portions located on said glove along opposed lateral edges of said palm surface to permit the glove to be worn on either the right or left hand of said wearer wherein the thumb of the wearer fits in one of the two holes.

* * * * *